US 8,838,405 B2

(12) United States Patent
Kitazawa et al.

(10) Patent No.: US 8,838,405 B2
(45) Date of Patent: *Sep. 16, 2014

(54) ULTRASONIC INSPECTION EQUIPMENT AND ULTRASONIC INSPECTION METHOD

(71) Applicant: Hitachi, Ltd., Tokyo (JP)

(72) Inventors: So Kitazawa, Mito (JP); Naoyuki Kono, Mito (JP); Atsushi Baba, Tokai (JP)

(73) Assignee: Mitsubishi Hitachi Power Systems, Ltd., Kanagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/049,731

(22) Filed: Oct. 9, 2013

(65) Prior Publication Data

US 2014/0035911 A1    Feb. 6, 2014

Related U.S. Application Data

(63) Continuation of application No. 12/472,873, filed on May 27, 2009, now Pat. No. 8,583,393.

(30) Foreign Application Priority Data

May 30, 2008    (JP) .................................. 2008-142192

(51) Int. Cl.
| | |
|---|---|
| G10K 11/00 | (2006.01) |
| G01N 29/06 | (2006.01) |
| G01N 29/04 | (2006.01) |
| G06T 19/20 | (2011.01) |

(52) U.S. Cl.
CPC ................ G01N 29/04 (2013.01); G01N 29/06 (2013.01); G06T 19/20 (2013.01)
USPC ........... 702/103; 702/108; 702/127; 702/152; 702/171

(58) Field of Classification Search
CPC .............. G06T 2201/005; G06T 19/20; G06T 2200/04
USPC ............... 702/33–36, 56, 108, 113–115, 127, 702/150–153, 159, 183, 171; 345/7–9, 345/418–427, 619, 629–641, 672–673
See application file for complete search history.

(56) References Cited

U.S. PATENT DOCUMENTS

| | | | |
|---|---|---|---|
| 5,475,613 | A | 12/1995 | Itoga et al. |
| 5,926,568 | A | 7/1999 | Chaney et al. |

(Continued)

FOREIGN PATENT DOCUMENTS

| | | |
|---|---|---|
| EP | 1 813 934 A1 | 8/2007 |
| JP | 3-94154 A | 4/1991 |

(Continued)

OTHER PUBLICATIONS

N. Kondo et al., Digital Signal Processing Series, vol. 12, Digital Signal Processing in Measurement Sensor, pp. 143-186, May 20, 1993. (partial translation attached).

(Continued)

*Primary Examiner* — Mischita Henson
(74) *Attorney, Agent, or Firm* — Mattingly & Malur, PC

(57) ABSTRACT

Ultrasonic inspection equipment facilitates alignment of display positions of three-dimensional ultrasonic inspection data and three-dimensional shape data, and quickly discriminates between a defect echo and an inner-wall echo. A computer 102A has a position correction function of correcting a relative display position between three-dimensional shape data and three-dimensional ultrasonic inspection data. A display position of the three-dimensional ultrasonic inspection data or that of the three-dimensional shape data is moved by a norm of a mean vector along the mean vector that is calculated from a plurality of vectors defined by a plurality of points selected in the three-dimensional ultrasonic inspection data and by a plurality of points selected in the three-dimensional shape data. The three-dimensional shape data and the three-dimensional ultrasonic inspection data are displayed in such a manner as to be superimposed on each other on a three-dimensional display unit 103C.

6 Claims, 8 Drawing Sheets

(56) References Cited

U.S. PATENT DOCUMENTS

| | | |
|---|---|---|
| 7,380,456 B2 | 6/2008 | Karasawa et al. |
| 7,454,973 B2 | 11/2008 | Baba et al. |
| 2005/0183505 A1 | 8/2005 | Kono et al. |
| 2006/0219013 A1 | 10/2006 | Baba et al. |
| 2008/0245150 A1 | 10/2008 | Katayama et al. |
| 2010/0106431 A1 | 4/2010 | Baba et al. |
| 2010/0185090 A1 | 7/2010 | Suzuki et al. |
| 2012/0137778 A1 | 6/2012 | Kitazawa et al. |
| 2013/0197824 A1 | 8/2013 | Baba et al. |
| 2013/0281897 A1 | 10/2013 | Hoffmann et al. |
| 2014/0035911 A1 | 2/2014 | Kitazawa et al. |

FOREIGN PATENT DOCUMENTS

| | | |
|---|---|---|
| JP | 05-245146 A | 9/1993 |
| JP | 6-102258 A | 4/1994 |
| JP | 06-292666 A | 10/1994 |
| JP | 2002-275802 A | 9/2002 |
| JP | 2002-306482 A | 10/2002 |
| JP | 2004-219287 A | 8/2004 |
| JP | 2004-302756 A | 10/2004 |
| JP | 2005-98768 A | 4/2005 |
| JP | 2006-275977 A | 10/2006 |
| JP | 2006-308566 A | 11/2006 |

OTHER PUBLICATIONS

A. Potts et al., Presentation and analysis enhancements of the NDT Workbench a software package for ultrasonic NDT data, Review of Progress in Quantituative Nondestruction Evaluation, vol. 19, AIP Conference Proceedings, vol. 509, pp. 741-748, 2000.

Japanese Office Action received in Japanese Application No. 2013-077758 dated Jun. 3, 2014.

ULTRASONIC INSPECTION EQUIPMENT AND ULTRASONIC INSPECTION METHOD

This application is a continuation of U.S. patent application Ser. No. 12/472,873, filed May 27, 2009, the disclosure of which is incorporated herein in its entirety.

BACKGROUND OF THE INVENTION

1. Field of the Invention

The present invention relates to ultrasonic inspection equipment and method for performing ultrasonic inspection that is a kind of non-destructive examination, and more particularly to ultrasonic inspection equipment and method that use an array-probe ultrasonic sensor.

2. Description of the Related Art

In the field of ultrasonic inspection methods for inspecting various kinds of structural materials, an inspection method for imaging an internal state of a target to be inspected in a short period of time with high accuracy to inspect the target has been developed in recent years. Such an inspection method for imaging is typified by a phased array method, a synthetic aperture focusing technique, and the like (for example, refer to non-patent document 1).

The phased array method uses a so-called array-probe ultrasonic sensor having a plurality of piezoelectric vibration elements arrayed therein. The phased array method is based on the principles that wavefronts of ultrasonic waves individually transmitted from the piezoelectric vibration elements interfere with one another to form a composite wavefront, which then propagates. Therefore, by delaying the ultrasonic-wave transmission timing of each of the piezoelectric vibration elements so as to shift the timing of each ultrasonic wave, an incident angle of each ultrasonic wave can be controlled, thereby making it possible to focus the ultrasonic waves.

In addition, upon reception of ultrasonic waves, a reflection ultrasonic wave received by each of the piezoelectric vibration elements is shifted prior to its addition. Thus, as is the case with the transmission of ultrasonic waves, an incident angle of the received ultrasonic wave can be controlled. Also it is possible to receive the focused ultrasonic waves.

In general, the following methods are known as the phased array method: the linear scan method in which piezoelectric vibration elements of a one-dimensional array sensor are rectilinearly scanned; and the sector scan method in which transmission and receiving directions of an ultrasonic wave are changed in sector-like fashion. In addition, if a two-dimensional array sensor having piezoelectric vibration elements arrayed in a lattice-shaped pattern is used, ultrasonic waves can be three-dimensionally focused at any position, thereby providing a scan method that is suitable for a target to be inspected. Both of the above-described methods are capable of: scanning an ultrasonic wave at high speed without moving an array-probe ultrasonic sensor; and optionally controlling an incident angle of an ultrasonic wave and a position of the depth of focus without replacing an array-probe ultrasonic sensor. The linear scan method and the sector scan method are techniques that enable high-speed, high-accuracy inspection.

Next, the principle on which the synthetic aperture focusing technique is based is as follows. When an ultrasonic wave is transmitted in such a manner that wave motion of the ultrasonic wave widely diffuses into a target to be inspected, and a reflected ultrasonic wave signal of the ultrasonic wave is received, a position of a defect, which is a sound source of the received reflected ultrasonic wave, exists along a circular arc whose radius is the propagation distance of the reflected ultrasonic wave with a position of a piezoelectric vibration element which has transmitted and received the ultrasonic wave defined as the center of the circular arc. Based on the principle, an ultrasonic wave is transmitted and is received while the piezoelectric vibration element is successively moved, and each received waveform at respective positions of the piezoelectric vibration element is calculated by a computer so as to extend a waveform in the shape of a circular arc. As a result, intersection points of the circular arcs are concentrated on the position of a defect that is an ultrasonic-wave reflection source, thereby making it possible to identify the position of the defect. How the computer performs the calculation for the above process is described in the non-patent document 1.

With the above-described methods, each of which employs a sensor in which a plurality of piezoelectric vibration elements are arrayed, it is possible to three-dimensionally obtain a reflected ultrasonic wave signal indicative of a defect without movement of the sensor. However, in order to identify a three-dimensional reflection position from the reflected ultrasonic wave signal, for example, the following estimation is required: estimating the reflection position from a plurality of two-dimensional images of the reflection intensity distribution, positions of the two-dimensional images spatially differing from one another; or estimating the reflection position by converting the reflection intensity distribution into three-dimensional data, and then by three-dimensionally displaying the converted data.

For example, in the case of the linear scan and the sector scan in the phased array method, a plurality of two-dimensional reflection intensity images according to known scanning pitch can be acquired. Accordingly, a direction in which a reflected wave occurs can be identified by displaying images on a screen while the images are successively switched. However, there are limits to apply this method to some three-dimensional scanning other than the above-described scanning.

In such a case, reflected ultrasonic wave signals from a plurality of directions are subjected to interpolation processing or the like to create three-dimensional lattice-shaped data. The three-dimensional lattice-shaped data obtained is displayed as an image using a method such as volume rendering and surface rendering. There is also a method in which reflected ultrasonic wave signals are displayed as a three-dimensional point group without converting the reflected ultrasonic wave signals into lattice-shaped data. In any case, because the reflected ultrasonic wave signals are stored as three-dimensional ultrasonic inspection data, an inspector can check the three-dimensional ultrasonic inspection data from any direction after measurement (for example, refer to non-patent document 2).

However, it is difficult to judge only from the three-dimensional ultrasonic inspection data whether a peak of the reflection intensity distribution results from the reflection on an end face or a boundary surface of a target to be inspected or from the reflection on a defect. In particular, in the case of a complicatedly shaped target to be inspected, a large number of reflected ultrasonic wave signals (inner-wall echoes) resulting from such a shape are generated. Therefore, it is difficult even for an expert to discriminate between an inner-wall echo and a defect echo. However, software is developed that is capable of displaying three-dimensional shape data of a target to be inspected together with three-dimensional ultrasonic inspection data. Superimposing these two pieces of data on each other to make a comparison between them facilitates the discrimination between an inner-wall echo and an echo resulting from a defect (defect echo). Incidentally, data that has been separately created by general-purpose CAD (Computer Aided Design) is often read and used as three-dimensional shape data (for example, refer to the non-patent document 2).

Cited references are as follows:
Patent document 1:
JP-A-6-102258
Non-patent document 1:
"Norimasa KONDO, Yoshimasa OHASHI, Akiro SANEMORI, Digital Signal Processing Series, Vol. 12 [Digital Signal Processing in Measurement•Sensor], PP. 143-186, May 20, 1993, Published by Shokodo
Non-patent document 2:
Potts, A.; McNab, A.; Reilly, D.; Toft, M., "Presentation and analysis enhancements of the NDT Workbench a software package for ultrasonic NDT data", REVIEW OF PROGRESS IN QUANTITATIVE NONDESTRUCTIVE EVALUATION; Volume 19, AlP Conference Proceedings, Volume 509, pp. 741-748 (2000)

SUMMARY OF THE INVENTION

However, because three-dimensional ultrasonic inspection data and three-dimensional shape data are usually made in separate coordinate systems, correction of display positions is always required to superimpose on each other these pieces of data are. Further, a theoretical value and an actually measured value of the sound velocity are used to display the three-dimensional ultrasonic inspection data. However, because the theoretical value differs from the actually measured value in a target to be inspected, correction of display scales is also required. If the correction of display positions and the correction of display scales are not correctly performed, correlation of the three-dimensional ultrasonic inspection data with the three-dimensional shape data cannot be confirmed. This makes impossible to discriminate between an inner-wall echo and a defect echo. Heretofore, an inspector inputs information about the position correction and the sound velocity correction through a display unit, or directly processes three-dimensional ultrasonic inspection data and three-dimensional shape data. The inspector need repeat the correction work until the discrimination between an inner-wall echo and a defect echo is attained. It is disadvantageous to take a huge amount of time for such correction work.

Incidentally, it is known that two-dimensional ultrasonic inspection data and two-dimensional shape data are displayed with these pieces of data superimposed on each other (for example, refer to lines 34 through 40 on the right column in page 6 of the patent document 1). The patent document 1 does not describe a specific technique for superimposing these pieces of data on each other. However, the patent document 1 describes that the pieces of data are superimposed on each other by establishing the coincidence between coordinates of an origin point of the two-dimensional ultrasonic inspection data and coordinates of an origin point of the two-dimensional shape data. However, in general, the origin point of the two-dimensional ultrasonic inspection data often differs from the origin point of the two-dimensional shape data. Accordingly, even if the coordinates of the origin point of the two-dimensional ultrasonic inspection data simply coincide with the coordinates of the origin point of the two-dimensional shape data, both of data cannot be successfully superimposed on each other. Moreover, the patent document 1 relates to the superimposition of two-dimensional ultrasonic inspection data and two-dimensional shape data. When the patent application described in the patent document 1 was filed, there was no technique for acquiring three-dimensional ultrasonic inspection data. Therefore, the superimposition of three-dimensional ultrasonic inspection data and three-dimensional shape data was not known. Differently from the superimposition of two-dimensional ultrasonic inspection data and two-dimensional shape data, for the superimposition of three-dimensional ultrasonic inspection data and three-dimensional shape data tilts of both data need be taken into consideration.

An object of the present invention is to provide ultrasonic inspection equipment and method which facilitate alignment of display positions of three-dimensional ultrasonic inspection data and three-dimensional shape data, and which are capable of quickly discriminating between a defect echo and an inner-wall echo.

(1) In order to achieve the above-described object, according to one aspect of the present invention, there is provided ultrasonic inspection equipment comprising:

an array-probe ultrasonic sensor including a plurality of piezoelectric vibration elements;

a pulser for supplying each of the piezoelectric vibration elements of the array-probe ultrasonic sensor with a transmission signal;

a receiver for receiving a signal from each of the piezoelectric vibration elements of the array-probe ultrasonic sensor;

a delay control unit for setting a delay time for the transmission signal and a delay time for the received signal differently for respective piezoelectric vibration elements;

a data storage unit for storing a waveform of an ultrasonic wave received by the array-probe ultrasonic sensor;

a computer for image processing, the computer generating three-dimensional ultrasonic inspection data from the waveform recorded by the data storage unit; and a three-dimensional display unit for displaying three-dimensional shape data and the three-dimensional ultrasonic inspection data;

wherein the computer includes position correction means for correcting a relative display position of the three-dimensional shape data and that of the three-dimensional ultrasonic inspection data; and the position correction means is adapted to move a position at which the three-dimensional ultrasonic inspection data is displayed or a position at which the three-dimensional shape data is displayed by a norm of a mean vector based on the mean vector, and to then display the three-dimensional shape data and the three-dimensional ultrasonic inspection data on the three-dimensional display unit in such a manner as to be superimposed on each other, wherein the mean vector is calculated from a plurality of vectors defined by a plurality of points selected in the three-dimensional ultrasonic inspection data and by a plurality of points selected in the three-dimensional shape data, the points selected in the three-dimensional shape data corresponding to the respective points selected in the three-dimensional ultrasonic inspection data.

The above-described configuration facilitates the alignment of display positions of three-dimensional ultrasonic inspection data and three-dimensional shape data. This makes it possible to quickly discriminate between a defect echo and an inner-wall echo.

(2) In the above-described item (1), preferably, the computer includes scale correction means for correcting a relative display scale between the three-dimensional shape data and the three-dimensional ultrasonic inspection data; and the scale correction means corrects a relative display scale between the three-dimensional ultrasonic inspection data and the three-dimensional shape data such that an absolute value of the distance between coordinates of two points selected in the three-dimensional ultrasonic inspection data coincides with an absolute value of the distance between coordinates of two points selected in the three-dimensional shape data.

(3) In the above-described item (1), preferably, when a plurality of points are selected from the three-dimensional ultrasonic inspection data, the position correction means displays data points existing within a specified range of the three-dimensional ultrasonic inspection data on the three-dimensional display unit in order of decreasing absolute value of the data points.

(4) In the above-described item (1), preferably, the computer includes data creation means for creating three-dimensional shape data such that the three-dimensional shape data is displayed in such a manner as to be superimposed on the three-dimensional ultrasonic inspection data.

(5) In the above-described item (1), preferably, the computer displays a plane indicating a cross section at an optional position of the three-dimensional ultrasonic inspection data on the three-dimensional display unit together with the three-dimensional ultrasonic inspection data.

(6) In order to achieve the above-described object, according to another aspect of the present invention, there is provided an ultrasonic inspection method comprising the steps of:

moving a position at which the three-dimensional ultrasonic inspection data is displayed or a position at which the three-dimensional shape data is displayed by a norm of a mean vector based on the mean vector, and then displaying the three-dimensional shape data and the three-dimensional ultrasonic inspection data, wherein the mean vector is calculated from a plurality of vectors defined by a plurality of points selected in the three-dimensional ultrasonic inspection data created from a plurality of ultrasonic wave waveforms received by an array-probe ultrasonic sensor and by a plurality of points selected in the three-dimensional shape data, the points selected in the three-dimensional shape data corresponding to the respective points selected in the three-dimensional ultrasonic inspection data.

The above-described method facilitates the alignment of display positions of three-dimensional ultrasonic inspection data and three-dimensional shape data. This makes it possible to quickly discriminate between a defect echo and an inner-wall echo.

(7) In the above-described item (6), preferably, the ultrasonic inspection method further comprises the step of correcting a relative display scale between the three-dimensional ultrasonic inspection data and the three-dimensional shape data such that the sum total of absolute values of the distance between coordinates of two points selected in the three-dimensional ultrasonic inspection data coincides with the sum total of absolute values of the distance between coordinates of two points selected in the three-dimensional shape data, the three-dimensional ultrasonic inspection data being created from the plurality of ultrasonic wave waveforms received by the array-probe ultrasonic sensor.

According to the present invention, the alignment of display positions of three-dimensional ultrasonic inspection data and three-dimensional shape data is facilitated. This makes it possible to quickly discriminate between a defect echo and an inner-wall echo.

DESCRIPTION OF THE PREFERRED EMBODIMENTS

A configuration of ultrasonic inspection equipment and operation thereof according to one embodiment of the present invention will be described below with reference to FIGS. 1 through 11.

First of all, a configuration of ultrasonic inspection equipment according to this embodiment will be described with reference to FIG. 1.

Figure 1:
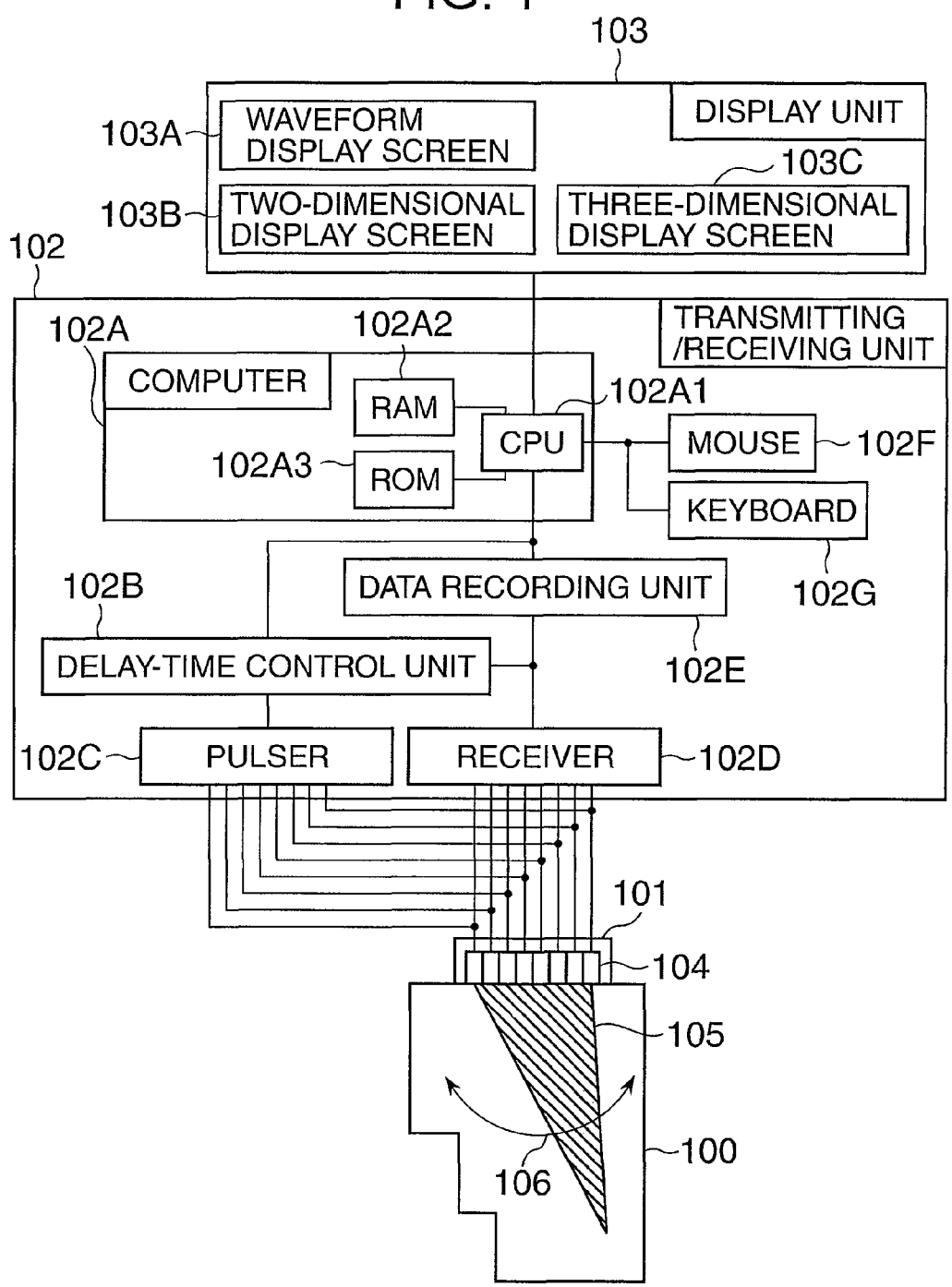
FIG. 1 is a system block diagram illustrating a configuration of ultrasonic inspection equipment according to one embodiment of the present invention.

FIG. 1 is a system block diagram illustrating the configuration of the ultrasonic inspection equipment according to one embodiment of the present invention.

The ultrasonic inspection equipment according to this embodiment includes: an array-probe ultrasonic sensor 101 for emitting an ultrasonic wave toward a target to be inspected 100; a transmitting/receiving unit 102; and a display unit 103 for displaying a received signal and an inspection image.

As described in the figure, the array-probe ultrasonic sensor 101 is basically constituted of a plurality of piezoelectric vibration elements 104, each of which generates an ultrasonic wave and then receives the ultrasonic wave. The array-probe ultrasonic sensor 101 is disposed on an inspection surface of the target to be inspected 100. The array-probe ultrasonic sensor 101 then generates an ultrasonic wave 105 in response to a driving signal supplied from the transmitting/receiving unit 102 so that the ultrasonic wave 105 propagates into the target to be inspected 100. As a result, the array-probe ultrasonic sensor 101 detects a reflected wave of the ultrasonic wave 105 therefrom, and then inputs a received signal into the transmitting/receiving unit 102.

The transmitting/receiving unit 102 transmits and receives the ultrasonic wave generated by the array-probe ultrasonic sensor 101. The transmitting/receiving unit 102 includes a computer 102A, a delay-time control unit 102B, a pulser 102C, a receiver 102D, a data storage unit 102E, a mouse 102F, and a keyboard 102G. The pulser 102C supplies the array-probe ultrasonic sensor 101 with a driving signal. Then, when the receiver 102D receives a signal from the array-probe ultrasonic sensor 101, the receiver 102D handles the received signal.

The computer 102A basically includes a CPU 102A1, a RAM 102A2, and ROM 102A3. A program for controlling the CPU 102A1 is written to the ROM 102A3. According to this program, the CPU 102A1 reads external data required by the data storage unit 102E, or transmits/receives data to/from the RAM 102A2 while computation is performed. In addition, the CPU 102A1 outputs handled data to the data storage unit 102E if necessary.

Moreover, the CPU 102A1 controls the delay-time control unit 102B, the pulser 102C, and the receiver 102D so that required operation is achieved. The delay-time control unit 102B controls both the timing of a driving signal output from the pulser 102C and the input timing of the received signal received by the receiver 102D. Thus the operation of the array-probe ultrasonic sensor 101 is performed based on the phased array method.

Here, in the operation of the array-probe ultrasonic sensor 101 based on the phased array method described above, the focal depth and incident angle 106 of the ultrasonic wave 105 are controlled so as to transmit an ultrasonic wave and then to receive the ultrasonic wave. Thus, the received signal is supplied from the receiver 102D to the data storage unit 102E. Next, the data storage unit 102E handles the supplied received signal, and then records the handled data as recorded data, and also transmits the handled data to the computer 102A. On the receipt of the data, the computer 102A combines waveforms obtained by the piezoelectric vibration elements in response to the delay time, and then performs interpolation processing suitable for the waveforms of the ultrasonic wave on an incident angle basis. The computer 102A then creates the following data: two-dimensional ultrasonic inspection data in a pixel format in which a two-dimensional square lattice which is called a "pixel" is used as a unit; and three-dimensional ultrasonic inspection data in a voxel format in which a three-dimensional cubic lattice which is called a "voxel" is used as a unit. The computer 102A controls to convert these pieces of data into images to display the images on the display unit 103.

The display unit 103 includes: a two-dimensional display screen 103B for displaying two-dimensional ultrasonic inspection data; a three-dimensional display screen 103C for displaying three-dimensional ultrasonic inspection data; and a waveform display screen 103A for displaying waveform signals of the piezoelectric vibration elements. FIG. 1 illustrates only one display unit 103. However, the waveform display screen 103A, the two-dimensional display screen 103B, and the three-dimensional display screen 103C may also be displayed and shared among a plurality of display units.

Three-dimensional ultrasonic inspection data is displayed on the three-dimensional display screen 103C of the display unit 103. In this case, the three-dimensional ultrasonic inspection data can be displayed on an optional display scale through the operation of the mouse 102F and the keyboard 102G connected to the computer 102A. An inspector is allowed to input the magnification, which is used to change the display scale, as a numerical value from the keyboard 102G into the computer 102A. In addition, display color and transparency can also be optionally changed through the operation of the mouse 102F and the keyboard 102G. The display color can be changed in response to the reflection intensity. In this case, a plurality of display color patterns are prepared and so the inspector can select among them on the basis of the use of the three-dimensional ultrasonic inspection data.

It is to be noted that the three-dimensional drawing algorithm as described above is implemented in libraries such as OpenGL (registered trademark) and DirectX (registered trademark), and that the OpenGL and the DirectX are industry-standard graphics application programming interfaces (graphics API) used in graphics applications. When these graphics APIs are used in a program to give required information about an object to be displayed, such as a shape, a viewpoint, and a display position, a three-dimensional shape can be easily drawn at any position on the display unit with the color, transparency, and scale optionally selected.

In addition, concurrently with the three-dimensional ultrasonic inspection data, three-dimensional shape data indicating a shape of the target to be inspected 100 is displayed on the three-dimensional display screen 103C. The three-dimensional shape data is read from the outside of the computer 102A. Moreover, the inspector is also allowed to create the three-dimensional shape data on the three-dimensional display screen 103C by use of the mouse 102F and the keyboard 102G. How to create the three-dimensional shape data on the three-dimensional display screen 103C will be described later in detail with reference to FIG. 7.

In particular, when CAD (Computer Aided Design) data of the target to be inspected 100 is available, the CAD data can be read and displayed. A CAD data format is a data format that enables CAD software on the market to input and output data. For example, the CAD data uses the STL (Stereo Lithography) format that enables most of CAD software to read and output data. The STL format expressed a surface of an object as a set of a large number of triangles. A STL file includes surface normal vectors of these triangles, and coordinate values of three vertexes of each triangle. By drawing the plurality of triangles, it is easy to display the three-dimensional shape data 202 from a file in the STL format using the graphics APIs.

Further, a plurality of pieces of three-dimensional shape data can also be concurrently displayed on the three-dimensional display screen 103C. Irrespective of the three-dimensional ultrasonic inspection data, selected three-dimensional shape data can be displayed at any position on any scale from an optional viewpoint through the operation of the mouse 102F and the keyboard 102G, both of which are connected to the computer 102A.

In addition, the inspector can also optionally change each of the display color and the transparency irrespective of the three-dimensional ultrasonic inspection data through the operation of the mouse 102F and the keyboard 102G. As a result, even if the three-dimensional shape data and the three-dimensional ultrasonic inspection data overlap one another, these pieces of data can be displayed in such a manner that the inspector can view them easily. Moreover, show/hide of the three-dimensional shape data can be switched if necessary.

Usually, because a coordinate system of three-dimensional ultrasonic inspection data differs from that of three-dimensional shape data, both of them are displayed at totally different positions in an initial state in which these pieces of data are superimposed upon each other. Even if initial information including an incident position of a ultrasonic wave is provided, there is, for example, a small difference in sound velocity inside the target to be inspected between an actually measured value and a theoretical value. Therefore, it is necessary to correct a display position and a display scale.

As described above, the three-dimensional ultrasonic inspection data and the three-dimensional shape data can be displayed independently of each other at any positions on any scales. The inspector, therefore, can also make alignments by trial and error so that the three-dimensional ultrasonic inspection data and the three-dimensional shape data are displayed at desired relative positions on desired scales. However, because the above correction work requires much time and effort, the use of a position correction function and a scale correction function makes the correction work becomes much easier, which will be described below.

Next, a position correction method for correcting a position of three-dimensional ultrasonic inspection data and that of three-dimensional shape data by ultrasonic inspection equipment according to this embodiment will be described with reference to FIGS. 2 through 4.

Figure 2:
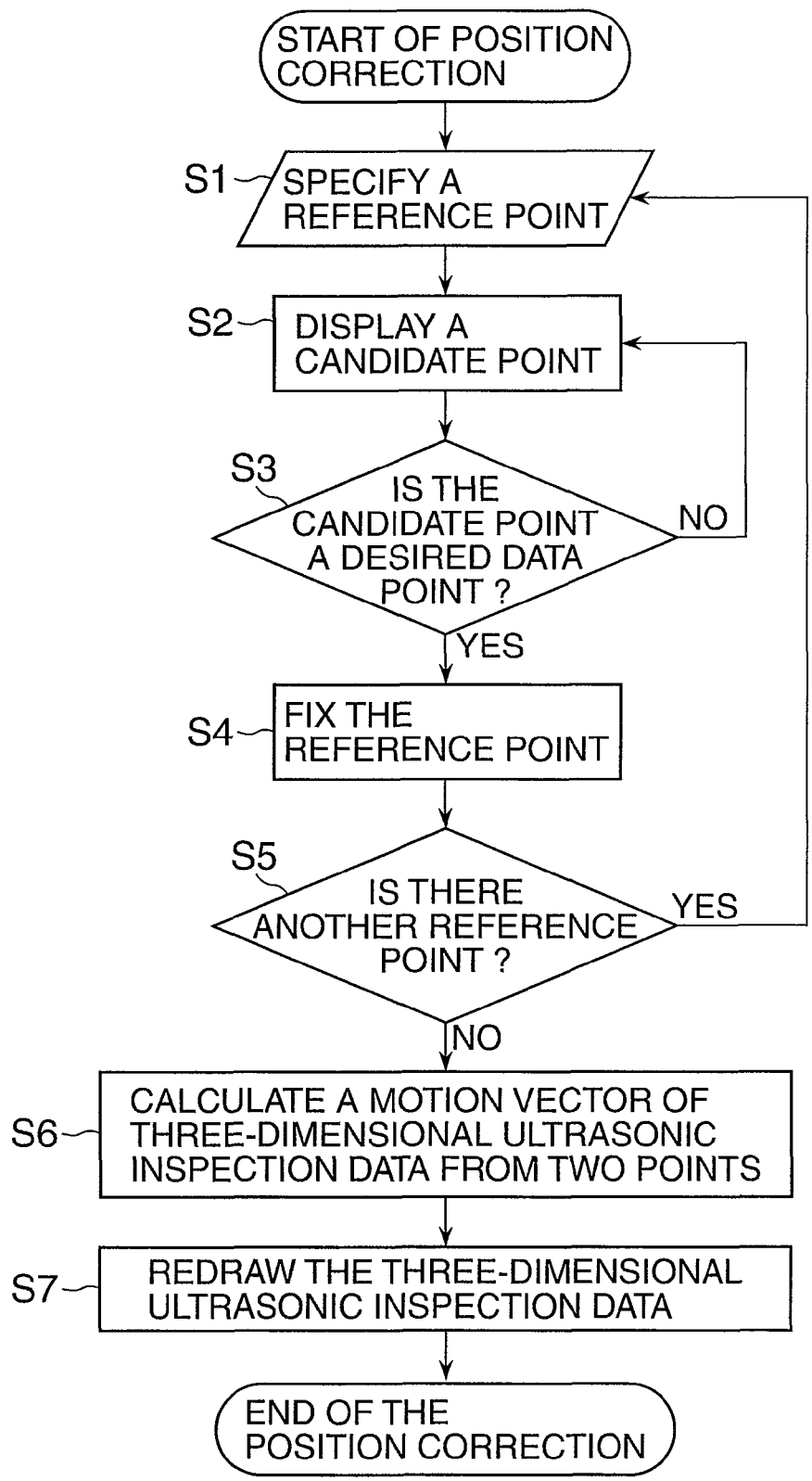
FIG. 2 is a flowchart illustrating processing executed based on the position correction method for correcting a position of three-dimensional ultrasonic inspection data and that of three-dimensional shape data by the ultrasonic inspection equipment according to one embodiment of the present invention.

FIG. 2 is a flowchart illustrating processing executed based on the position correction method for correcting a position of three-dimensional ultrasonic inspection data and that of three-dimensional shape data by ultrasonic inspection equipment according to one embodiment of the present invention. FIGS. 3 and 4 are diagrams each illustrating the position correction method for correcting a position of three-dimensional ultrasonic inspection data and that of three-dimensional shape data by ultrasonic inspection equipment according to one embodiment of the present invention.

The position correction method is a function of making a correction such that three-dimensional ultrasonic inspection data coincide with three-dimensional shape data at a desired position.

In a step S1 shown in FIG. 2, an inspector specifies a reference point. For example, as shown in FIG. 3, if the inspector wants to move three-dimensional ultrasonic inspection data 201 in parallel so that coordinates of an optional point 201A in the three-dimensional ultrasonic inspection data 201 coincide with coordinates of an optional point 202A in three-dimensional shape data 202, the inspector first selects the reference point 201A and the reference point 202A with the mouse 102F while viewing the three-dimensional display screen 103C.

How to select these points on the three-dimensional display screen 103C will be described as below. First, a position to be specified as a first reference point in the three-dimensional ultrasonic inspection data 201 is clicked with the mouse 102F on the three-dimensional display screen 103C; and the clicked point is then diagonally dragged with the mouse 102F, so that a rectangle area is selected. Points included in the three-dimensional ultrasonic inspection data 201, which are drawn in the rectangular area, are read into the RAM 102A2 of the computer. Each of the points has an identification number. Incidentally, identification numbers are given to data points in order of decreasing absolute value of data point (in descending order of intensity) among pieces of ultrasonic inspection data included in the rectangular area.

In a step S2 shown in FIG. 2, when points included in a minute area in plural, the CPU 102A1 displays a first point included in these points on the three-dimensional display screen 103C as a candidate point.

In a step S3, the inspector specifies the candidate point through the operation of the mouse 102F or the keyboard 102G. However, when the candidate point is not a desired data point, the process returns to the step S2 where the next candidate point is displayed in order of identification numbers on the screen with the color thereof successively changed.

In a step S4, when the desired data point is displayed as a candidate, the inspector accepts the selection of this point through the operation of the mouse 102F or the keyboard 102G.

Next, in a step S5 shown in FIG. 2, a judgment is made as to whether or not there is another reference point. Here, because it is also necessary to select the first reference point included in the three-dimensional shape data 202, the processing in the steps S1 through S4 is performed to select the first reference point 202A included in the three-dimensional shape data 202 corresponding to the first reference point 201A included in the ultrasonic inspection data 201 shown in FIG. 3, and then to accept the selection of the first reference point 202A. For example, if the three-dimensional shape data 202 is STL format data, a point to be selected is any one of vertexes of a triangle forming the three-dimensional shape data 202. Algorithm for reading an identification number of a selected point and positional information about the selected point into the RAM 102A2 is already implemented by graphics API such as OpenGL. Accordingly, the use of functions provided in the graphics API makes it possible to easily implement the algorithm.

Further, according to this embodiment, at least two reference points are used in each of the ultrasonic inspection data 201 and the three-dimensional shape data 202. Therefore, the second reference point 202B included in the three-dimensional shape data 202 corresponding to the second reference point 201B included in the ultrasonic inspection data 201 is selected, and the selection of the second reference point 202B is then accepted.

Here, the reference points to be selected are, for example, an ultrasonic wave incident point 201B in the three-dimensional ultrasonic inspection data 201 and a sensor mounting point (ultrasonic wave incident position) 202B in the three-dimensional shape data 202. In another case, the reference points to be selected are, for example, a peak point of an inner-wall echo whose cause is known (for example, the point 201A) and points surrounding the peak point in the three-dimensional ultrasonic inspection data 201, and a point on an end face of the three-dimensional shape data 202 (for example, the point 202A). Besides, for example, the following reference points shown in FIG. 3 can also be used as reference points: the reference point 201C and the reference point 201D included in the three-dimensional ultrasonic inspection data 201; and the reference point 202C and the reference point 202D included in the three-dimensional shape data 202. With the increase in the numbers of reference points, the degree of coincidence between the three-dimensional ultrasonic inspection data and the three-dimensional shape data can be increased.

Combinations of corresponding reference points are automatically set as follows: the reference point 201A and the reference point 202A; the reference point 201B and the reference point 202B; the reference point 201C and the reference point 202C; and the reference point 201D and the reference point 202D. In this case, a selected reference point is displayed on the three-dimensional display screen 103C with the color of the selected reference point changed.

Next, in a step S6 shown in FIG. 2, the CPU 102A1 calculates a motion vector of the three-dimensional ultrasonic inspection data from the plurality of reference points. Here, on the assumptions that the number of combinations of a point in the three-dimensional ultrasonic inspection data 201 and its corresponding point in the three-dimensional shape data 202 is N, and that in the i-th combination, coordinates of a point and those of its corresponding point are (xi1, Yi1, zi1) and (xi2, Yi2, zi2) respectively, the motion vector is an average of motion vectors determined based on the combinations. The motion vector is calculated by the following equation (1):

$$\vec{V} = \left( \sum_{i=1}^{N} \frac{Xi2 - Xi1}{N}, \sum_{i=1}^{N} \frac{Yi2 - Yi1}{N}, \sum_{i=1}^{N} \frac{Zi2 - Zi1}{N} \right) \quad \text{Eq. 1}$$

Next, in a step S7, the CPU 102A1 controls to perform parallel and rotational movement of the three-dimensional ultrasonic inspection data 201 by the motion vector based on the equation (1). The CPU 102A1 then redraws the three-dimensional ultrasonic inspection data 201 at a move-to-position as shown in FIG. 4. Incidentally, the three-dimensional shape data 202 may also be moved.

Next, a scale correction method for correcting a scale of three-dimensional ultrasonic inspection data and that of three-dimensional shape data by the ultrasonic inspection equipment according to this embodiment will be described with reference to FIGS. 5 and 6.

Figure 5:
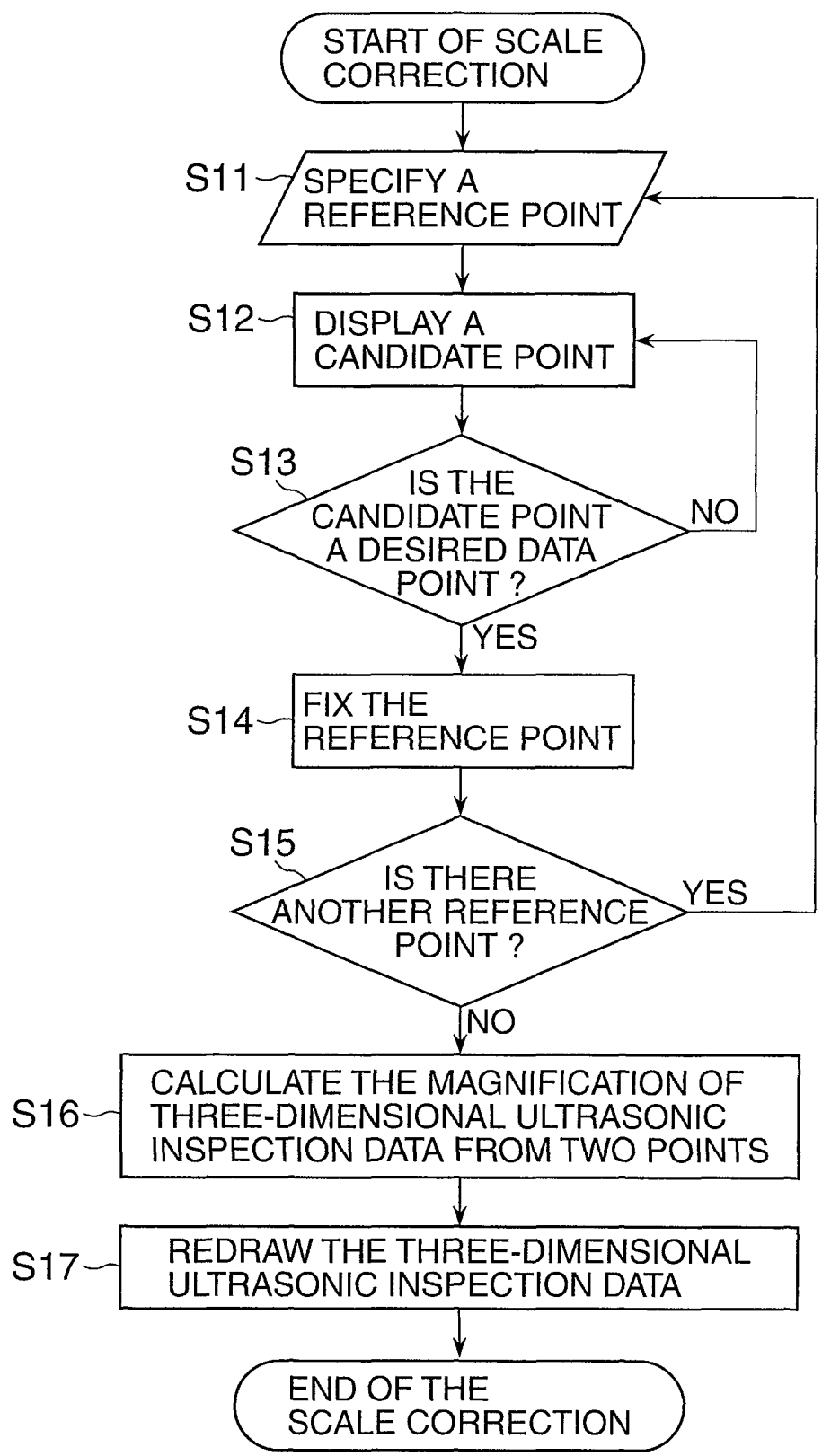
FIG. 5 is a flowchart illustrating processing executed based on the scale correction method for correcting a scale of three-dimensional ultrasonic inspection data and that of three-dimensional shape data by the ultrasonic inspection equipment according to one embodiment of the present invention.

FIG. 5 is a flowchart illustrating processing executed based on the scale correction method for correcting a scale of three-dimensional ultrasonic inspection data and that of three-dimensional shape data by the ultrasonic inspection equipment according to one embodiment of the present invention. FIG. 6 is a diagram illustrating the scale correction method for correcting a scale of three-dimensional ultrasonic inspection data and that of three-dimensional shape data by the ultrasonic inspection equipment according to one embodiment of the present invention.

Figure 3:
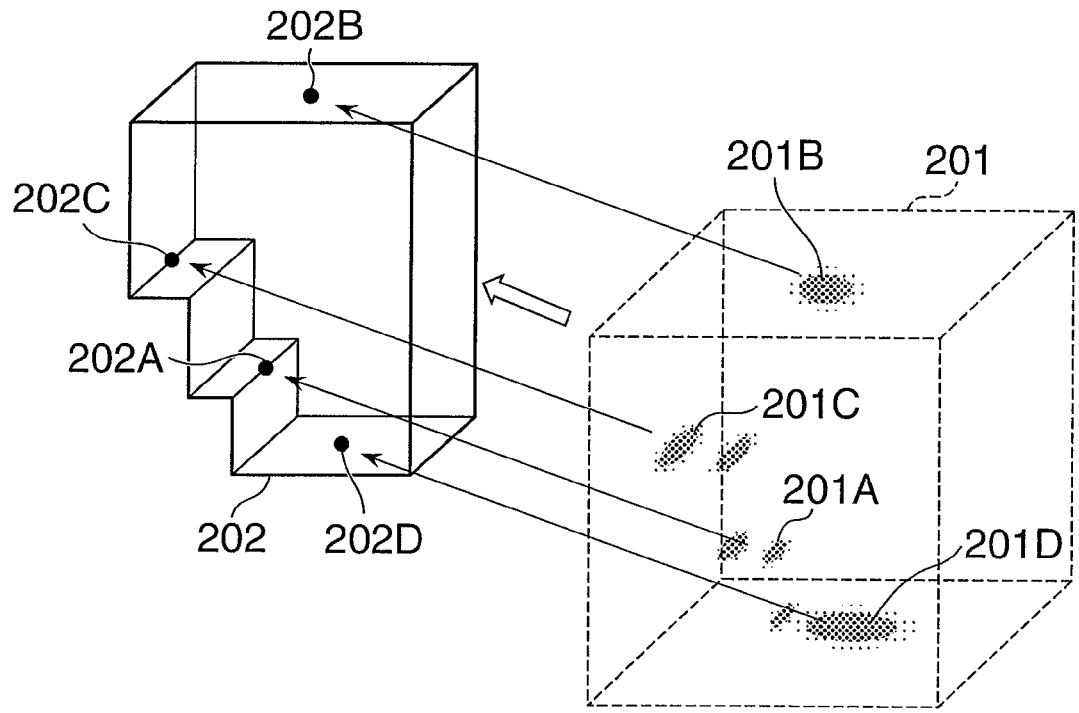
FIG. 3 is a diagram illustrating the position correction method for correcting a position of three-dimensional ultrasonic inspection data and that of three-dimensional shape data by the ultrasonic inspection equipment according to one embodiment of the present invention.
Figure 4:
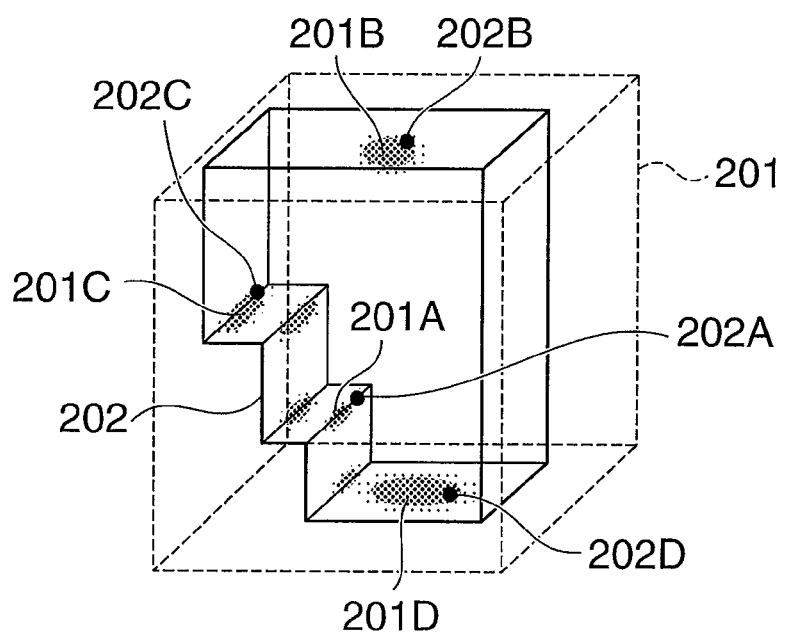
FIG. 4 is a diagram illustrating the position correction method for correcting a position of three-dimensional ultrasonic inspection data and that of three-dimensional shape data by the ultrasonic inspection equipment according to one embodiment of the present invention.

When the degree of coincidence between the three-dimensional ultrasonic inspection data 201 and the three-dimensional shape data 202 is not sufficiently increased only if the position correction function described with reference to FIGS. 2 through 4 is performed, a scale correction function is used.

Figure 6:
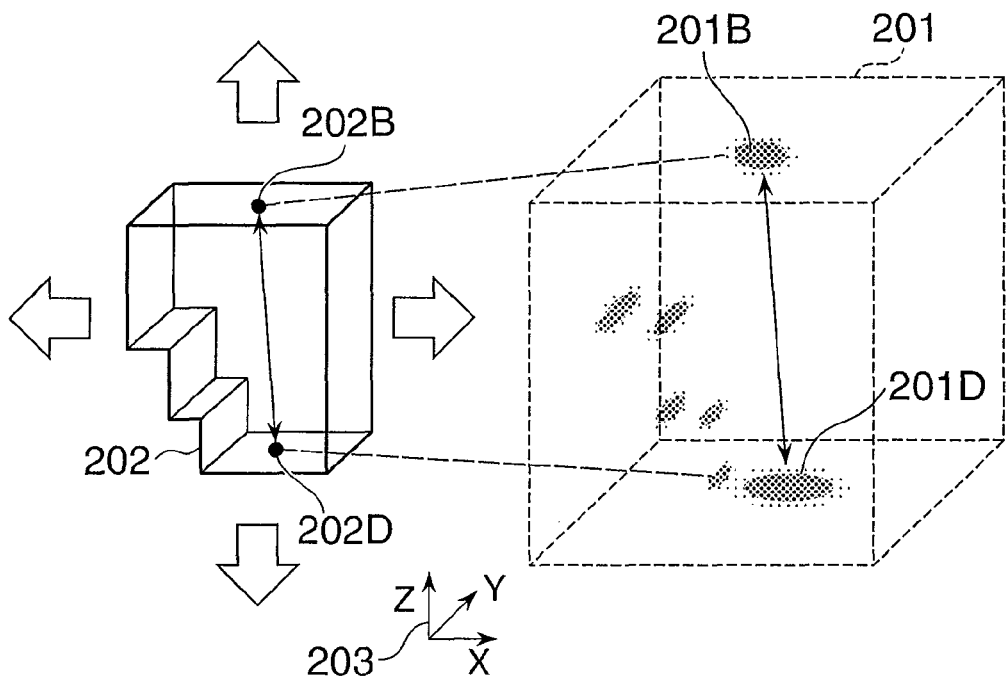
FIG. 6 is a diagram illustrating the scale correction method for correcting a scale of three-dimensional ultrasonic inspection data and that of three-dimensional shape data by the ultrasonic inspection equipment according to one embodiment of the present invention.

What will be described next is a case where, for example, as shown in FIG. 6, the inspector wants to change a display scale of the three-dimensional ultrasonic inspection data 201 in such a manner that the distance between the reference point 201B and the reference point 201D included in the three-dimensional ultrasonic inspection data 201 coincides with the distance between the corresponding reference point 202B and the corresponding reference point 202D included in the three-dimensional shape data 202.

Processing in steps S11 through S15 shown in FIG. 5 is the same as that in the steps S1 through S5 shown in FIG. 2.

Accordingly, in the steps S11 through S15 shown in FIG. 5, the inspector makes selections on the three-dimensional display screen 103C with the mouse 102F in the following order: first selecting two points included in the three-dimensional ultrasonic inspection data 201; and then selecting two points included in the three-dimensional shape data 202.

Incidentally, selections may be made in any order in each of the three-dimensional ultrasonic inspection data 201 and the three-dimensional shape data 202. In this case, a selected reference point is displayed on the three-dimensional display screen 103C with the color of the selected reference point changed. Here, the reference points to be selected are, for example, an ultrasonic wave incident point 201B in the three-dimensional ultrasonic inspection data 201 and a sensor mounting point 202B in the three-dimensional shape data 202. In another case, the reference points to be selected are, for example, a peak point of an inner-wall echo whose cause is known (for example, the point 201D) and points surrounding the peak point in the three-dimensional ultrasonic inspection data 201, and a point on an end face of the three-dimensional shape data 202 (for example, the point 202D).

Next, in a step S16, the CPU 102A1 calculates the magnification of the three-dimensional ultrasonic inspection data from these reference points. For example, on the assumption that coordinates of the point 201B, the point 201D are (X1B, Y1B, Z1B), (X1D, Y1D, Z1D) respectively, whereas coordinates of the point 202B, the point 202D are (X2B, Y2B, Z2B), (X2D, Y2D, Z2D) respectively, the magnification is calculated by the following equation (2):

$$S = \frac{\sqrt{(X2D - X2B)^2 + (Y2D - Y2B)^2 + (Z2D - Z2B)^2}}{\sqrt{(X1D - X1B)^2 + (Y1D - Y1B)^2 + (Z1D - Z1B)^2}} \quad \text{Eq. 2}$$

Next, in a step S17, the CPU 102A1 redraws the three-dimensional ultrasonic inspection data 201 on a scale that has been corrected by the magnification calculated by use of the equation (2). Incidentally, in contrast with the above, the three-dimensional shape data 202 may also be corrected by a reduction ratio that is an inverse number of the magnification calculated by use of the equation (2), before the three-dimensional shape data 202 is redrawn.

Next, a creation method for creating three-dimensional shape data by the ultrasonic inspection equipment according to this embodiment will be described with reference to FIGS. 7 through 9.

Figure 7:
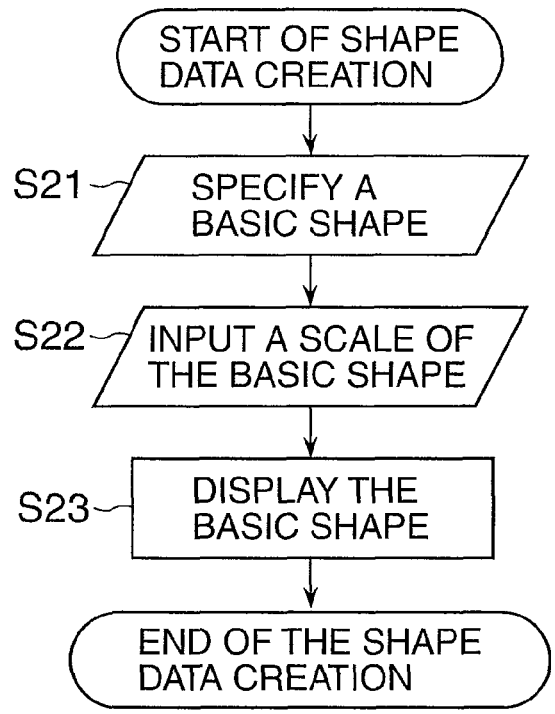
FIG. 7 is a flowchart illustrating processing executed based on the creating method for creating three-dimensional shape data by the ultrasonic inspection equipment according to one embodiment of the present invention.

FIG. 7 is a flowchart illustrating processing executed based on the creating method for creating three-dimensional shape data by the ultrasonic inspection equipment according to one embodiment of the present invention. FIGS. 8 and 9 are diagrams each illustrating the creation method for creating three-dimensional shape data by the ultrasonic inspection equipment according to one embodiment of the present invention.

As described above, the three-dimensional shape data 202 is not necessarily read from the outside of the computer 102A. The inspector is also allowed to create the three-dimensional shape data 202 on the computer 102A through the operation of the mouse 102F and the keyboard 102G while viewing the three-dimensional display screen 103C.

In a step S21 shown in FIG. 7, the inspector selects a basic shape which the inspector wants to display on an operation screen. The basic shape is, for example, a plane, a cube, a cuboid, a sphere, a cone, or a cylinder.

Next, in a step S22, the inspector inputs a scale of the basic shape. An optional numerical value can be inputted as the scale.

In a step S23, the CPU 102A1 draws the selected basic shape at an initial position on the three-dimensional display screen 103C. It is to be noted that the initial position may be set at any position.

After the selected basic shape is drawn, the position and scale of the basic shape relative to those of the three-dimensional ultrasonic inspection data 201 are aligned to a desired state by using the position correction function and the scale correction function. By repeating the above operation for a plurality of basic shapes, an external shape of the target to be inspected 100 can be roughly formed. As a matter of course, only representative portions of the target to be inspected (for example, an inspection surface, a bottom surface, and a side surface) may be drawn.

Incidentally, because graphics API such as OpenGL has a function of drawing shapes including a plane, a cube, a cuboid, a sphere, a cone, and a cylinder, these shapes can be easily drawn by use of the graphics API.

Figure 8:
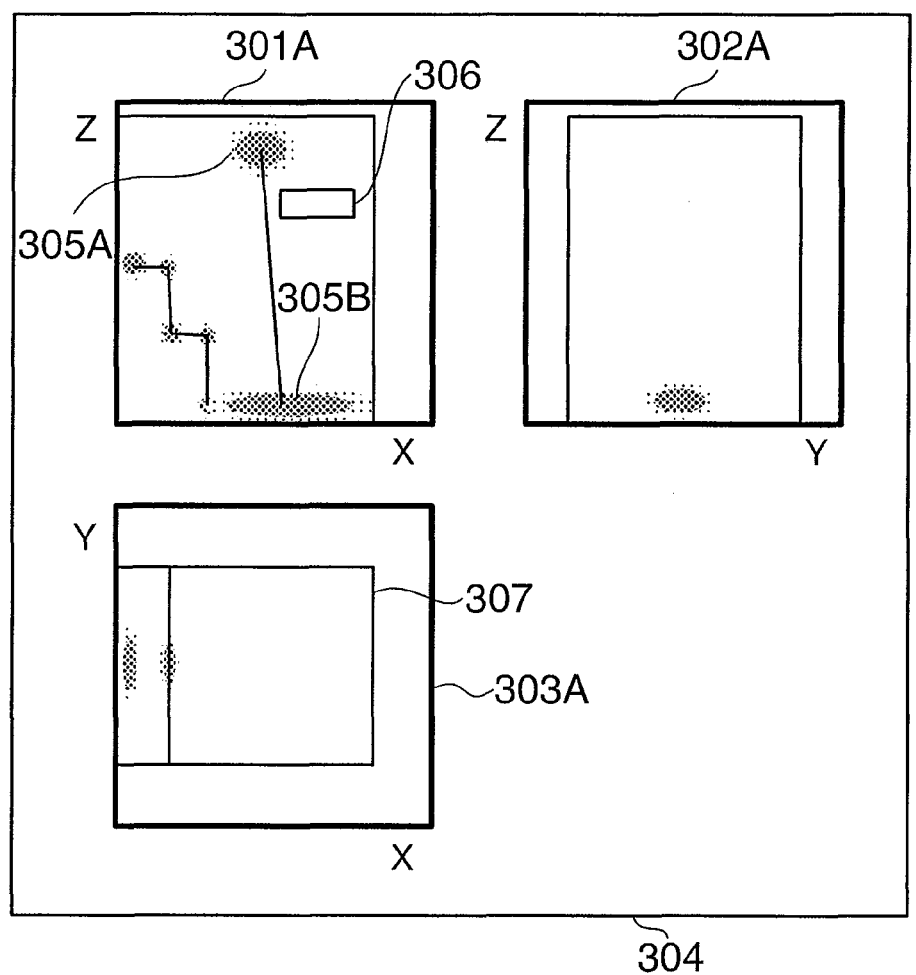
FIG. 8 is a diagram illustrating the creation method for creating three-dimensional shape data by the ultrasonic inspection equipment according to one embodiment of the present invention.
Figure 9:
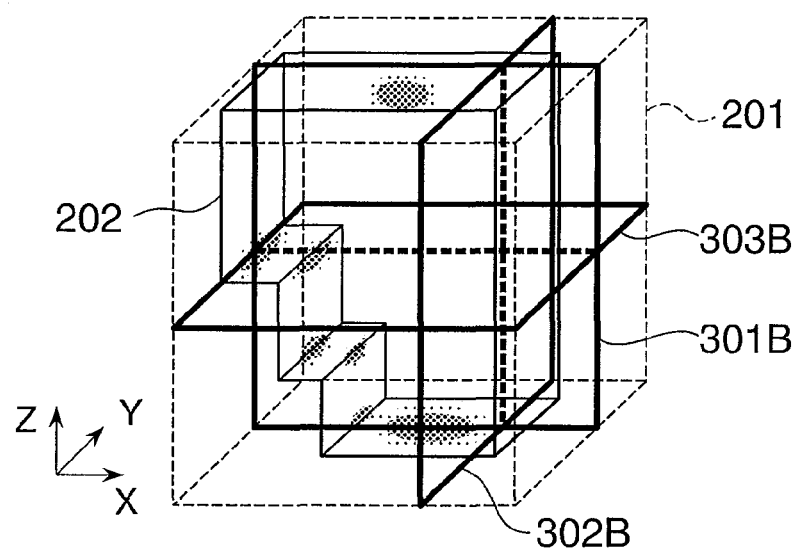
FIG. 9 is a diagram illustrating the creation method for creating three-dimensional shape data by the ultrasonic inspection equipment according to one embodiment of the present invention.

Here, as shown in FIG. 8, the three-dimensional display screen 103C has a cross-section display screen 304 for displaying the reflection intensity distribution of planes (for example, a X-Y plane, a Y-Z plane, and a Z-X plane), each of which is parallel to two axes of a coordinate system of the three-dimensional ultrasonic inspection data 201. The cross-section display screen 304 includes a screen 301A, a screen 302A, and a screen 303A, which display the reflection intensity distribution of the X-Y plane, the Y-Z plane, and the Z-X plane respectively. For example, in screen 303A, the portion of the three-dimensional shape shape data 307 in the X-Y plane is shown. Further, as shown in FIG. 9, planes 301B, 302B, and 303B, which indicate positions of the above-described planes, are displayed on the three-dimensional display screen 103C together with the three-dimensional ultrasonic inspection data 201 and the three-dimensional shape data 202. This enables the inspector to easily check which portion of a cross section is displayed.

In addition, because a plane indicating a cross section at an optional position of the three-dimensional ultrasonic inspection data is displayed on a three-dimensional display unit together with the three-dimensional ultrasonic inspection data, the inspector can efficiently compare the three-dimensional ultrasonic inspection data with the three-dimensional shape data so as to discriminate between an inner-wall echo and a defect echo. This makes it possible to easily and quickly identify a position of a defect of a target to be inspected.

For example, when the three-dimensional ultrasonic inspection data is voxel format data, the three-dimensional ultrasonic inspection data has a data structure that is equally spaced along X, Y, Z axes. Therefore, by specifying a value of X on a voxel basis, the reflection intensity distribution of a Y-Z plane corresponding to X (that is to say, the distribution of voxel values) can be easily determined. Similarly, the reflection intensity distribution of a Z-X plane, and that of a X-Y plane, can be easily determined by specifying a value of Y and Z respectively. As shown in FIG. 9, the planes 301B, 302B, 303B can be easily displayed by using a plane display function of graphics API such as OpenGL.

Next, a distance measuring method for measuring the distance between optional two points by the ultrasonic inspection equipment according to this embodiment will be described with reference to FIG. 10.

Figure 10:
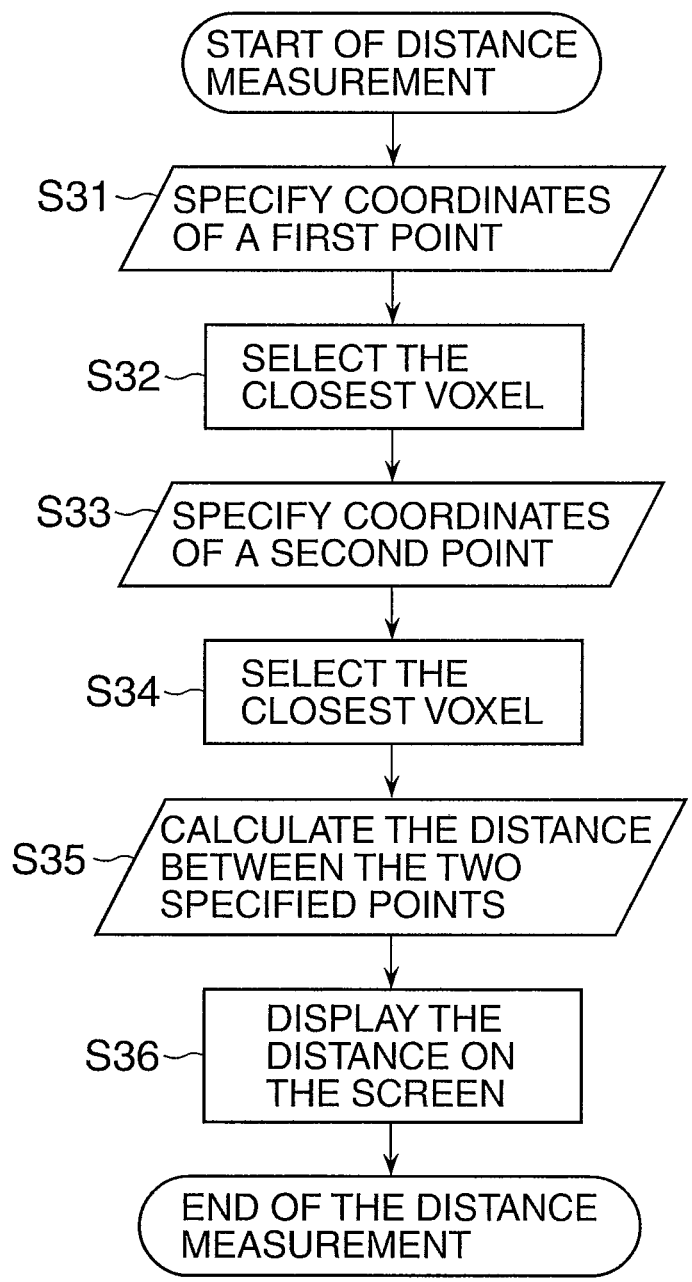
FIG. 10 is a flowchart illustrating processing executed based on a distance measuring method for measuring the distance between optional two points by the ultrasonic inspection equipment according to one embodiment of the present invention.

FIG. 10 is a flowchart illustrating processing executed based on the distance measuring method for measuring the distance between optional two points by the ultrasonic inspection equipment according to one embodiment of the present invention.

Referring to FIG. 8, when the inspector specifies two optional points (for example, points 305A and 305B) with the mouse 102F connected to the computer 102A on the cross-section display screen 304, the distance 306 between the two points is displayed at, for example, a position 306 in proximity to a specified point on the cross-section display screen 304. A method of specifying the points 305A and 305B is similar to that for specifying a point included in the three-dimensional ultrasonic inspection data and the three-dimensional shape data by use of the above-described graphics API such as OpenGL.

In a step S31 shown in FIG. 10, the inspector clicks a point 305A on the screen 301A with the mouse 102F.

Then, in a step S32, the CPU 102A1 selects a point whose coordinates are closest to those of the clicked point from among pixels included in a minute area having a specified area, the minute area including the clicked point. The CPU 102A1 then reads the coordinates of the selected point into the RAM 102A2 of the computer.

Similarly, in steps S33 and S34, the CPU 102A1 selects a point 305B, and then reads coordinates thereof into the RAM 102A2.

Next, in a step S35, the CPU 102A1 calculates the distance between the two selected points from the coordinates of the two selected points. In a step S36, the CPU 102A1 then displays the distance on a screen.

It is to be noted that the above processing is the same as that for the screen 302A or the screen 303A shown in FIG. 8.

Next, another configuration of the ultrasonic inspection equipment according to this embodiment will be described with reference to FIG. 11.

Figure 11:
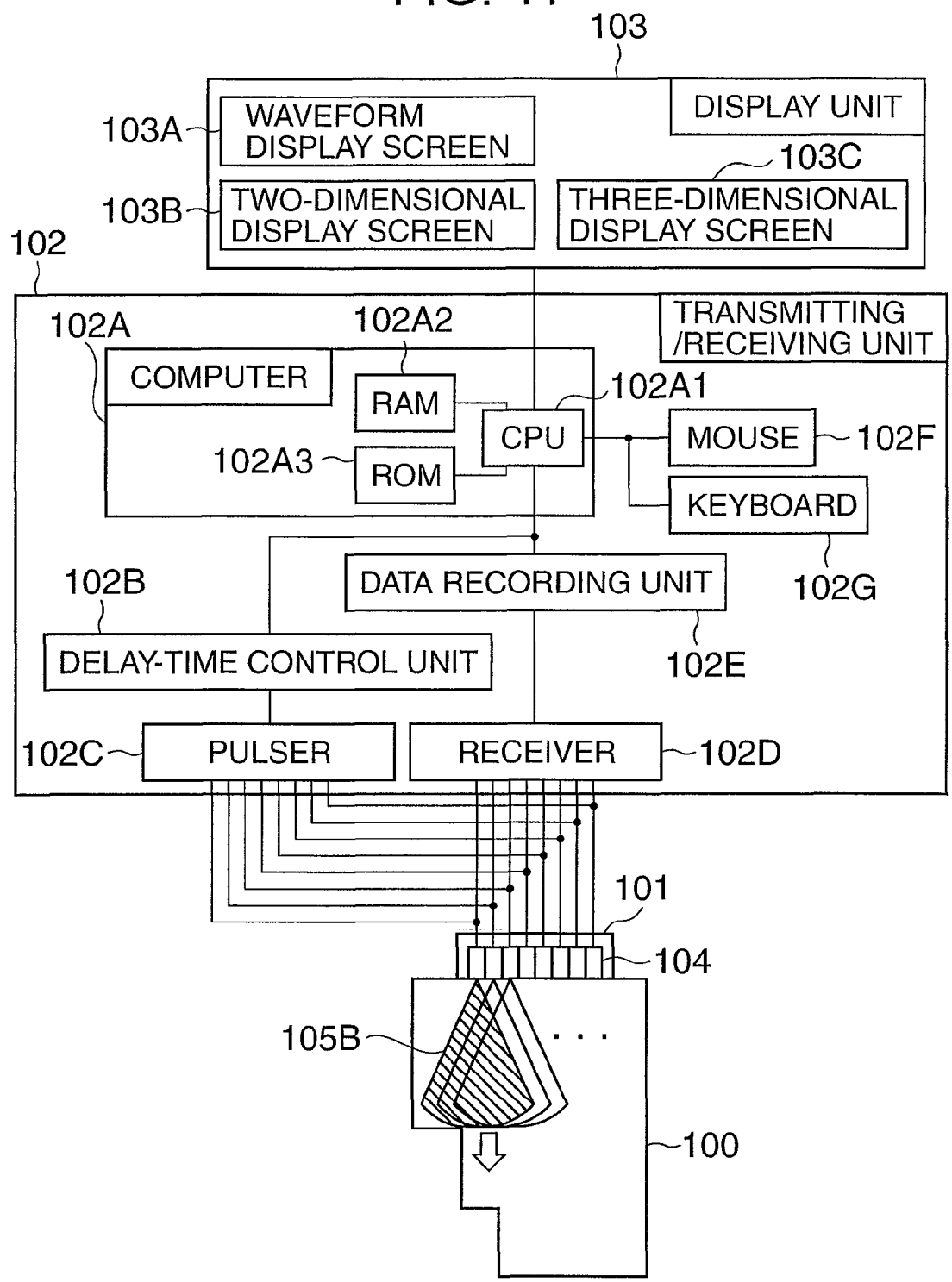
FIG. 11 is a system block diagram illustrating another configuration of ultrasonic inspection equipment according to one embodiment of the present invention.

FIG. 11 is a system block diagram illustrating another configuration of the ultrasonic inspection equipment according to one embodiment of the present invention.

The example shown in FIG. 1 shows a case where three-dimensional ultrasonic inspection data is obtained by a phased array method. The present invention, however, can also be applied to three-dimensional ultrasonic inspection data obtained by a method other than the phased array method (for example, a synthetic aperture focusing technique).

FIG. 11 is a diagram illustrating a configuration of ultrasonic inspection equipment based on the synthetic aperture focusing technique.

The ultrasonic inspection equipment according to this example includes: an array-probe ultrasonic sensor 101 for emitting an ultrasonic wave toward a target to be inspected 100; a transmitting/receiving unit 102; and a display unit 103 for displaying a received signal and an inspection image.

As described in the figure, the array-probe ultrasonic sensor 101 is basically constituted of a plurality of piezoelectric vibration elements 104, each of which generates an ultrasonic wave and then receives the ultrasonic wave. The array-probe ultrasonic sensor 101 is disposed on an inspection surface of the target to be inspected 100. The array-probe ultrasonic sensor 101 then generates an ultrasonic wave 105B in response to a driving signal supplied from the transmitting/receiving unit 102 so that the ultrasonic wave 105 propagates into the target to be inspected 100. As a result, the array-probe ultrasonic sensor 101 detects a reflected wave of the ultrasonic wave 105 therefrom, and then inputs a received signal into the transmitting/receiving unit 102.

Each of the piezoelectric vibration elements 104 of the array-probe ultrasonic sensor 101 is successively driven by a driving signal in the required timing to generate an ultrasonic wave. The driving signal is transmitted from a driving signal control unit through a pulser. Each of the piezoelectric vibration elements 104 then receives a reflected wave of the generated ultrasonic wave in a two-dimensional manner. The received signal is inputted into the receiver 102D of the transmitting/receiving unit 102.

In other words, the piezoelectric vibration elements 104 of the array-probe ultrasonic sensor 101 receive reflected waves of the ultrasonic waves generated by the piezoelectric vibration elements 104 respectively. The number of the reflected waves is equivalent to the total number of the piezoelectric vibration elements 104.

The signal inputted into the receiver 102D is successively recorded in the data storage unit 102E as recorded data. The computer 102A uses the recorded data to handle a waveform obtained by each of the piezoelectric vibration elements 104 such that the waveform is subjected to three-dimensional image processing based on the synthetic aperture focusing technique before the waveform is displayed on the display unit 103.

The computer 102A basically includes a CPU 102A1, a RAM 102A2, and ROM 102A3. A program for controlling the CPU 102A1 is written to the ROM 102A3. According to this program, the CPU 102A1 reads external data required by the data storage unit 102E, or transmits/receives data to/from the RAM 102A2 while computation is performed. In addition, the CPU 102A1 outputs handled data to the data storage unit 102E if necessary.

How to display the three-dimensional ultrasonic inspection data 201, which has been generated based on the synthetic aperture focusing technique by the computer 102A, together with the three-dimensional shape data 202 so as to handle the three-dimensional ultrasonic inspection data 201 is similar to the method described with reference to FIGS. 2 through 10.

As described above, according to this embodiment, the ultrasonic inspection equipment has the position correction function of correcting a relative display position of three-dimensional shape data and that of three-dimensional ultrasonic inspection data. Thus the inspector can efficiently compare the three-dimensional ultrasonic inspection data with the three-dimensional shape data so as to discriminate between an inner-wall echo and a defect echo, thereby making it possible to easily and quickly identify a position of a defect of a target to be inspected.

In addition, the ultrasonic inspection equipment has the scale correction function of correcting a relative display scale between three-dimensional shape data and three-dimensional ultrasonic inspection data. As a result, the inspector can efficiently compare the three-dimensional ultrasonic inspection data with the three-dimensional shape data so as to discriminate between an inner-wall echo and a defect echo, thereby making it possible to easily and quickly identify a position of a defect of a target to be inspected.

Moreover, because data points included in three-dimensional ultrasonic inspection data, which exist within a specified range, are displayed on the three-dimensional display unit in order of decreasing absolute value of data points, coordinates can be more easily specified to make corrections. The inspector, therefore, can efficiently compare the three-dimensional ultrasonic inspection data with the three-dimensional shape data so as to discriminate between an inner-wall echo and a defect echo, thereby making it possible to easily and quickly identify a position of a defect of a target to be inspected.

Further, because the ultrasonic inspection equipment has data creation means for creating three-dimensional shape data, the inspector can efficiently compare the three-dimensional ultrasonic inspection data with the three-dimensional shape data so as to discriminate between an inner-wall echo and a defect echo, thereby making it possible to easily and quickly identify a position of a defect of a target to be inspected.

Furthermore, because a plane indicating a cross section at an optional position of the three-dimensional ultrasonic inspection data is displayed on the three-dimensional display unit together with the three-dimensional ultrasonic inspection data, the inspector can efficiently compare the three-dimensional ultrasonic inspection data with the three-dimensional shape data so as to discriminate between an inner-wall echo and a defect echo, thereby making it possible to easily and quickly identify a position of a defect of a target to be inspected.

What is claimed is:

1. Ultrasonic inspection equipment comprising:
a computer for image processing, the computer generating three-dimensional ultrasonic inspection data as an inspection result of a target from a waveform of an ultrasonic wave received by an ultrasonic sensor;
a display unit for displaying three-dimensional shape data of the target and the three-dimensional ultrasonic inspection data;
wherein the computer includes a position correction part for correcting a relative display position of the three-dimensional shape data and that of the three-dimensional ultrasonic inspection data; and
the position correction part is configured to move a position at which the three-dimensional ultrasonic inspection data is displayed or a position at which the three-dimensional shape data is displayed by a norm of a mean vector based on the mean vector, and to then display the three-dimensional shape data and the three-dimensional ultrasonic inspection data on the display unit in such a manner as to be superimposed on each other, wherein the mean vector is calculated from a plurality of vectors defined by a plurality of points selected in the three-dimensional ultrasonic inspection data and by a plurality of points selected in the three-dimensional shape data, the points selected in the three-dimensional shape data corresponding to the respective points selected in the three-dimensional ultrasonic inspection data.

2. The ultrasonic inspection equipment according to claim 1, wherein the computer includes a processing part for measuring and displaying a distance between two points selected on a screen of the display unit.

3. The ultrasonic inspection equipment according to claim 2, wherein the processing part reads first coordinates of a point being closest to those of a first point among points in a minute area having a specified area around the first point selected on the screen of the display unit, reads second coordinates of a point among points in a minute area having the specified area around the second point selected on the screen of the display unit, and calculates and displays a distance between the first coordinates and the second coordinates.

4. An ultrasonic inspection method comprising the steps of:
creating three-dimensional ultrasonic inspection data as an inspection result of a target with an image processing unit from an ultrasonic wave waveform received by an ultrasonic sensor;
moving a position at which the three-dimensional ultrasonic inspection data is displayed or a position at which three-dimensional shape data of the target is displayed by a norm of a mean vector based on the mean vector; and
displaying the three-dimensional shape data and the three-dimensional ultrasonic inspection data on a display unit, wherein the mean vector is calculated from a plurality of vectors defined by a plurality of points selected in the three-dimensional ultrasonic inspection data and by a plurality of points selected in the three-dimensional shape data, the points selected in the three-dimensional shape data corresponding to the respective points selected in the three-dimensional ultrasonic inspection data.

5. The ultrasonic inspection method according to claim 4, further comprising the steps of measuring and displaying a distance between two points selected on a screen of the display unit.

6. The ultrasonic inspection method according to claim 5, wherein a distance between first coordinates and second coordinates is calculated and displayed on the screen of the display unit, the first coordinates of a point being closest to those of a first point among points in a minute area having a specified area around the first point selected on the screen of the display unit, second coordinates of a point being closest to those of a second point among points in a minute area having the specified area around the second point selected on the screen of the display unit.

* * * * *